(12) United States Patent
Petros

(10) Patent No.: US 10,426,594 B2
(45) Date of Patent: Oct. 1, 2019

(54) ANCHORING DEVICE AND ITS IMPLEMENTATION

(75) Inventor: Peter Emmanuel Petros, Claremont (AU)

(73) Assignee: KVINNO CENTRE PTY LTD, Claremont, Western Australia (AU)

( * ) Notice: Subject to any disclaimer, the term of this patent is extended or adjusted under 35 U.S.C. 154(b) by 315 days.

(21) Appl. No.: 13/362,462

(22) Filed: Jan. 31, 2012

(65) Prior Publication Data

US 2012/0190916 A1    Jul. 26, 2012

Related U.S. Application Data

(62) Division of application No. 10/524,701, filed as application No. PCT/AU03/01036 on Aug. 15, 2003, now Pat. No. 8,753,372.

(30) Foreign Application Priority Data

Aug. 13, 2002 (AU) ................. 2002951024
Oct. 17, 2002 (AU) ................. 2002952128
May 23, 2003 (AU) ................. 2003902559

(51) Int. Cl.
  *A61F 2/08*   (2006.01)
  *A61B 17/04*  (2006.01)
  *A61B 17/00*  (2006.01)

(52) U.S. Cl.
  CPC ........ *A61F 2/0805* (2013.01); *A61B 17/0401* (2013.01); *A61F 2/0811* (2013.01); *A61B 2017/00805* (2013.01); *A61B 2017/0409* (2013.01); *A61B 2017/0412* (2013.01); *A61B 2017/0414* (2013.01); *A61B 2017/0437* (2013.01); *A61B 2017/0464* (2013.01); *A61F 2002/0852* (2013.01); *A61F 2002/0888* (2013.01)

(58) Field of Classification Search
  CPC ...... A61B 17/0401; A61B 2017/00805; A61B 2017/0409; A61F 2/0805; A61F 2/0811
  USPC ......... 606/151, 232–233, 139, 144, 224, 75; 24/115, 132, 132 AA; 600/30, 37
  See application file for complete search history.

(56) References Cited

U.S. PATENT DOCUMENTS 5,242,457 A    9/1993  Akopov et al.
5,370,662 A   12/1994  Stone et al.
(Continued)

FOREIGN PATENT DOCUMENTS

EP    0558993    9/1993
EP    0713683    5/1996
(Continued)

OTHER PUBLICATIONS

Gyneideas; Portfolio, www.gyneideas.com/portfolio.htm; Oct. 31, 2003.

*Primary Examiner* — Vy Q Bui
(74) *Attorney, Agent, or Firm* — Gottlieb, Rackman & Reisman, P.C.

(57) ABSTRACT

A method of providing ligamentory like support between two spaced locations in the body of a patient comprising fixing an anchor in each location, connecting the anchors by a filamentary element, adjusting the tension of the filamentary element between the locations to establish the desired spatial relationship between the locations to provide at least a supplementary ligamentory support between the locations.

21 Claims, 20 Drawing Sheets

(56) References Cited

U.S. PATENT DOCUMENTS

| | | | |
|---|---|---|---|
| 5,417,712 | A | 5/1995 | Whittaker et al. |
| 5,423,860 | A | 6/1995 | Lizardi et al. |
| 5,662,654 | A | 9/1997 | Thompson |
| 5,702,397 | A | 12/1997 | Goble et al. |
| 5,891,168 | A | 4/1999 | Thal |
| 5,944,739 | A | 8/1999 | Zlock et al. |
| 5,961,014 | A * | 10/1999 | Knerr ............... A45F 3/04 224/153 |
| 6,015,428 | A * | 1/2000 | Pagedas ............... 606/232 |
| 6,066,160 | A | 5/2000 | Colvin et al. |
| 6,139,565 | A | 10/2000 | Stone et al. |
| 6,174,323 | B1 | 1/2001 | Biggs et al. |
| 6,334,446 | B1 | 1/2002 | Beyar |
| 6,451,024 | B1 * | 9/2002 | Thompson et al. ......... 606/104 |
| 6,599,311 | B1 | 7/2003 | Biggs et al. |
| 6,981,983 | B1 * | 1/2006 | Rosenblatt et al. ......... 606/216 |
| 7,326,213 | B2 * | 2/2008 | Benderev et al. .......... 606/139 |
| 2002/0065528 | A1 | 5/2002 | Clark et al. |
| 2003/0088250 | A1 | 5/2003 | Colleran et al. |
| 2003/0120309 | A1 | 6/2003 | Colleran et al. |
| 2003/0130669 | A1 * | 7/2003 | Damarati ............... 606/151 |

FOREIGN PATENT DOCUMENTS

| | | |
|---|---|---|
| FR | 2731610 | 9/1996 |
| JP | 08-196546 | 8/1996 |
| WO | 99/59477 | 11/1999 |
| WO | 01/67962 | 9/2001 |
| WO | 02/30293 | 4/2002 |

\* cited by examiner

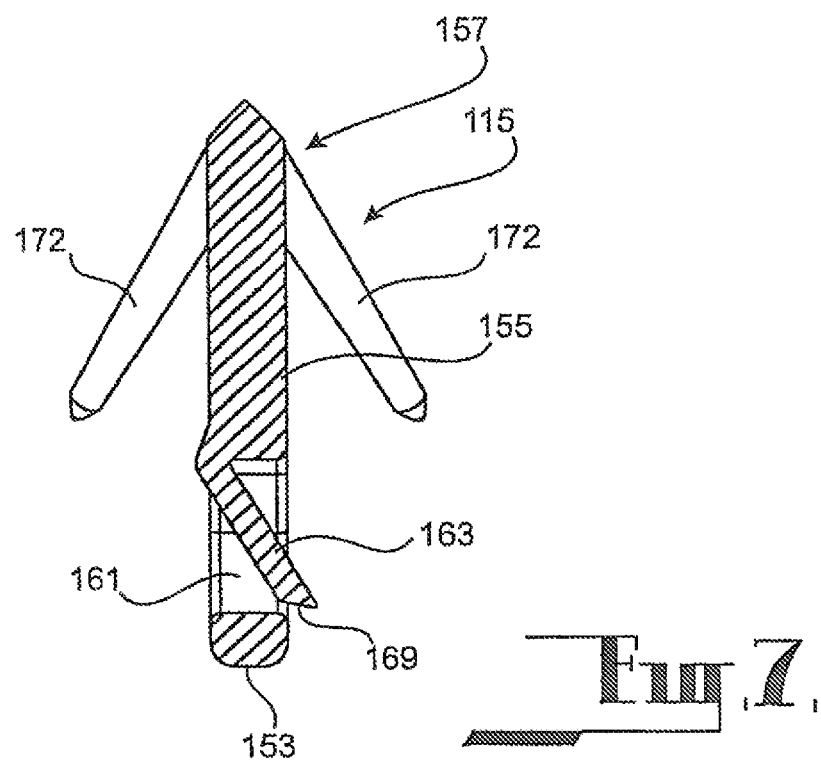
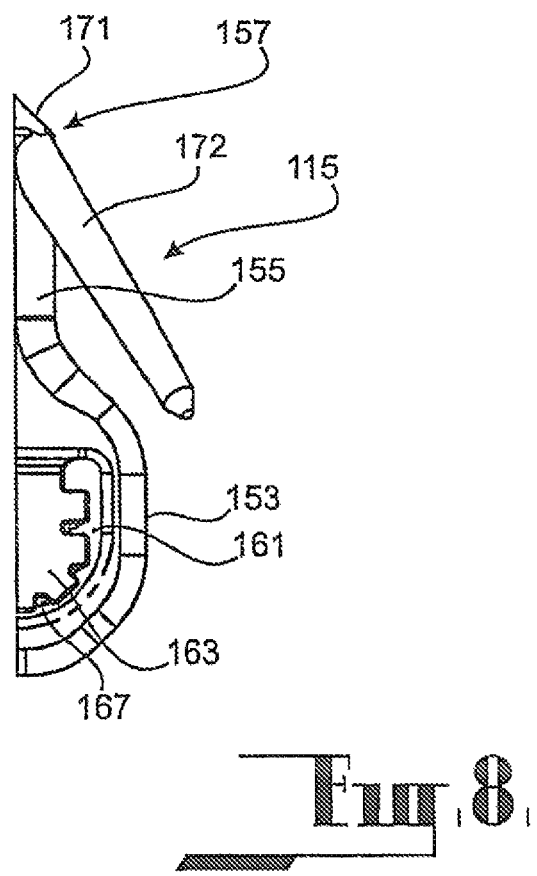

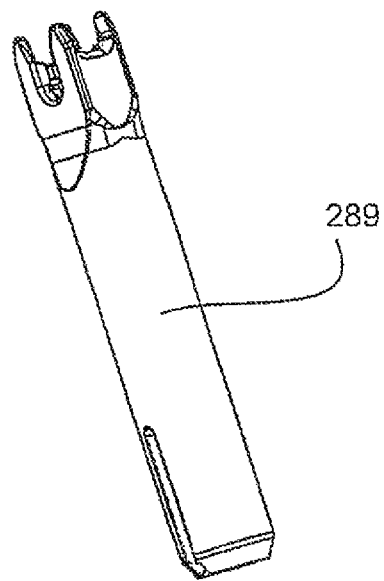
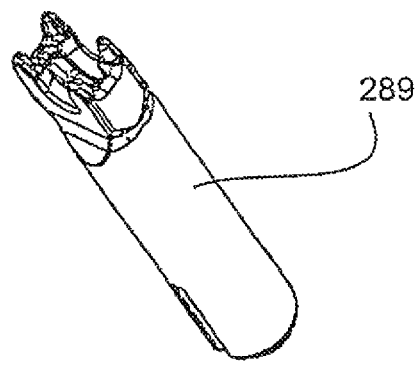
Fig. 16.

ANCHORING DEVICE AND ITS IMPLEMENTATION

RELATED APPLICATIONS

This application is a Division of U.S. application Ser. No. 10/524,701 filed Feb. 16, 2005, now pending.

This invention relates to an anchor which can be used in surgical procedures on both humans and animals.

BACKGROUND ART

The invention has application to a wide variety of surgical procedures and one such procedure relates to a method of resolving female incontinence, which involves insertion of a filament which is to be fixed to the ligamentous tissue to either side of the vagina in order to reconstitute the ligamentary support for the urethra and/or vaginal wall. In the past such filaments have either been fixed to the pubic bone or alternatively the rectus abdominous muscle or left "tension free" in that muscle.

The inventor is the principal author of an article entitled "Role of the Pelvic Floor in Bladder Neck Opening and Closure II: Vagina" which appeared in the International Urogynecology Journal (1997) 8:69-73. In that article it was identified the "connective tissue laxity in the vagina or its supporting ligaments is the prime cause of symptoms of stress, urgency and abnormal emptying". As a result in the case of a lax vagina, at least some of the muscular activity which is applied to maintain continence is taken up in resolving the vaginal laxity rather than control of the urethra. Therefore in rectifying the problem it is desirable to establish a situation in which the relationship between the existing muscular and ligamentory support can be reestablished.

DISCLOSURE OF THE INVENTION

Accordingly in one aspect the invention resides in a method of providing ligamentory like support between two spaced locations in the body of a patient wherein the locations comprise ligament and/or muscle tissue comprising fixing an anchor in each location, connecting the anchors by a filamentary element, adjusting the tension of the filamentary element between the locations to establish the desired spatial relationship between the locations to provide at least a supplementary ligamentory support between the locations.

According to a preferred feature of the invention the locations comprise ligament and/or muscle tissue.

According to a preferred feature of the invention the anchors are provided with a retaining means adapted to be able to retain the filamentary element in optimal tension between the anchors.

According to a preferred feature of the invention the retaining means enables movement of the filamentary element through the anchor to enable the length of the filamentary element between the locations to be shortened but to prevent movement of the filamentary element through the anchors to enable the length of the filamentary element between the applications to be increased.

According to a further preferred feature of the invention the filamentary element is not biodegradable over a period of time and is adapted to facilitate the growth of tissue between the locations to provide said ligamentory support between the locations.

According to a preferred feature of the invention the anchor comprises a head having a configuration facilitating insertion into the tissue and retention of the head in the tissue once inserted, the anchor further having a base which is intended to receive the filamentary element, said method comprising inserting the head of the anchor into the tissue with the base buried in the tissue.

According to a further preferred feature of the invention the head has a barbed configuration. According to a preferred feature of the invention the barbed configuration comprises a set of prongs extending in a divergent manner from the end of the head towards the base, said prongs being resiliently flexible along their length, said method comprising compressing the ends of the prongs towards each other prior to insertion of the head into the tissue, inserting the head into the tissue and releasing the ends of the prongs once the head is located in the tissue.

According to a further preferred feature of the invention the anchor is associated with a holder which is configured to retain the anchor with the head directed outwardly from the holder, the method comprising installing an anchor in the holder and placing the anchor in position in the tissue by means of the holder, subsequently disengaging the holder from the anchor. According to a preferred feature of the invention the filamentary element is installed in the anchor and the anchor is installed on the holder prior to insertion of the head into the tissue. According to a preferred feature of the invention the holder is adapted to receive and support the prongs in their compressed state, said method comprising releasing the prongs from engagement with the holder when the anchor is in position.

According to a further preferred feature of the invention the holder is associated with an insertion appliance, the insertion appliance having a shaft, one end of the shaft adapted to receive the holder, the other end of the shaft supporting the handle, an ejection means extending between the handle and the one end and having a bearing member at one end adapted to bear upon an anchor when installed in the holder, the handle provided with a manipulation member adapted to cause the bearing member to bear on the anchor and cause the displacement of the anchor from the holder, said method comprising locating the holder at the one end of the shaft, installing an anchor into the holder, placing the anchor in position in the tissue by manipulation of the appliance and on location of the anchor in the tissue, activation of the manipulation means to cause displacement of the anchor from the holder.

According to a preferred feature of the invention the spaced locations comprise the recto-vaginal ligaments or the arcus tendineus ligaments to each side of the vagina and the method resides in the re-establishing of the fascial support for the vagina, said method comprising fixing said anchors into the recto-vaginal ligaments or the arcus tendineus ligaments respectively to each side of the vagina, applying the filamentary element between the anchors and introducing the filamentary element into the fascial tissue such that with time it will become embodied with the fascia and optimally tensioning the filamentary element between the anchors.

According to a preferred feature of the invention the filamentary element is applied to at least one of the anchors prior to fixation. According to a preferred embodiment of the invention the filamentary element is applied to a pair of anchors at a spacing greater than that desired spatial relationship.

According to another aspect the invention resides in a tissue anchor formed of a material which is compatible for location in human and/or animal muscle and/or ligament tissue, the anchor comprising a base and a head, the head having a configuration to facilitate insertion of the head into tissue and retention of the head in the tissue once inserted, the base formed with an aperture adapted to receive a length of a filamentary element and permit slidable movement of the filamentary element through the aperture in one direction but to restrict movement of the filamentary element through the aperture in the opposite direction.

According to a preferred feature of the invention the aperture is associated with a locking element positioned to extend across the aperture to define a space between the locking element and an opposed edge of the aperture, said space being intended to receive the filamentary element, the locking member having one face proximate the one direction and another face proximate the opposite direction, the locking element intended to cooperate with the filamentary element when in position in the space to restrict the movement of the filamentary element in the opposite direction and to enable movement of the filamentary element in the one direction. According to a preferred feature the edge of the locking element defining the space is formed to engage the surface of the filamentary element when filamentary element is moved in the opposite direction. According to a preferred feature of the invention the edge is defined by a surface extending between the faces of the locking member, the surface being inclined away from the opposed edge of the aperture in the opposite direction. According to a preferred feature of the invention the edge is formed with slots which extend from the face proximate the one direction to at least an intermediate position across the surface. According to a preferred feature of the invention the face of the locking member proximate the one direction is formed as a recess inwardly of the edge. According to a preferred feature the locking member is inclined with respect to the base.

According to a preferred feature the space has a configuration substantially corresponding to the cross section of the filamentary element. According to a preferred feature of the invention the space has a configuration corresponding to the cross sectional configuration of the filamentary element when under longitudinal tension. According to a preferred feature of the invention the space has a part annular configuration. According to a preferred feature of the invention the opposed edge of the locking element which is remote from the head has a convex arcuate configuration. According to a preferred feature of the invention the space is located substantially centrally across the central longitudinal axis of the anchor.

According to a preferred feature of the invention the head has a barbed configuration. According to a preferred feature of the invention the barbed configuration of the head is defined by a set of prongs, said prongs being located in substantially equi-distant spacing around the central axis of the head, said prongs being divergent away from the end of the head in the direction of base.

According to a preferred feature of the invention the prongs are of a tapered configuration. According to a preferred feature of the invention the outer end of the prongs are pointed. According to a preferred feature of the invention the prongs are resiliently flexible along their length.

According to a further aspect the invention resides in a holder adapted to support the anchor as described above comprising a socket configured to clampingly receive the base, the socket being configured to allow access to the aperture, the clamping engagement between the holder and the base being such that on relative movement between the holder and the anchor the anchor is able to be disengaged from the holder.

According to a preferred feature of the invention the base has a substantially laminar-like configuration comprising two opposed substantially parallel faces.

According to a preferred feature of the invention the socket comprises a pair of spaced elements which receive opposed sides of the base with the aperture between the spaced elements.

According to a preferred feature of the invention the socket is defined by a set of boss elements which are configured to receive the free ends of the prongs of the anchor when compressed radially with respect to the central axis of the anchor.

According to a further aspect the invention resides in an insertion appliance comprising a shaft adapted to accommodate the holder as described above at one end, the other end of the shaft supporting a handle, an ejection means extending between the one end and the handle, a bearing member provided at the one end and a manipulation means provided adjacent the handle whereby on an anchor being installed in the holder and on activation of the manipulation means the bearing member will bear upon the anchor to move the anchor from engagement with the holder.

According to a preferred embodiment a holder of the form described above having an anchor of the form described above applied thereto are provided as a single element.

According to a preferred embodiment an insertion appliance of the form described above supporting a holder of the form described above having an anchor of the form described above applied thereto are provided as a single element.

The invention will be more fully understood in the light of the following description of several specific embodiments

BRIEF DESCRIPTION OF THE DRAWINGS

The description is made with reference to the accompanying drawings of which:

FIG. 7 is a sectional side elevation of an anchor according to the third embodiment;

FIG. 8 is a side elevation of an anchor according to the third embodiment;

FIG. 16 are isometric views of the cradle like support according to the fourth embodiment;

DETAILED DESCRIPTION OF SPECIFIC EMBODIMENTS

The method according to the first embodiment comprises utilisation of an anchor of the form described below as the second and third embodiments. The anchor provides a means of attaching a filament into muscle and/or ligamentary tissue. The anchor has a head which is able to be embedded into the tissue whereby once it is so embedded the anchor is retained in position. In addition the anchor has an attachment means which is able to receive and support a filament whereby the filament can slide through the attachment means in one direction but is restrained from slidable movement in the opposite direction.

It is the purpose of the procedure according to the embodiment to incorporate into the fascial tissue, which is located above and below the vaginal wall, a supporting filamentary element which is supported at either end from either the recto-vaginal ligaments or the arcus tendineus (A.T.F.P.) ligaments located to each side of the vagina.

Figure 1:
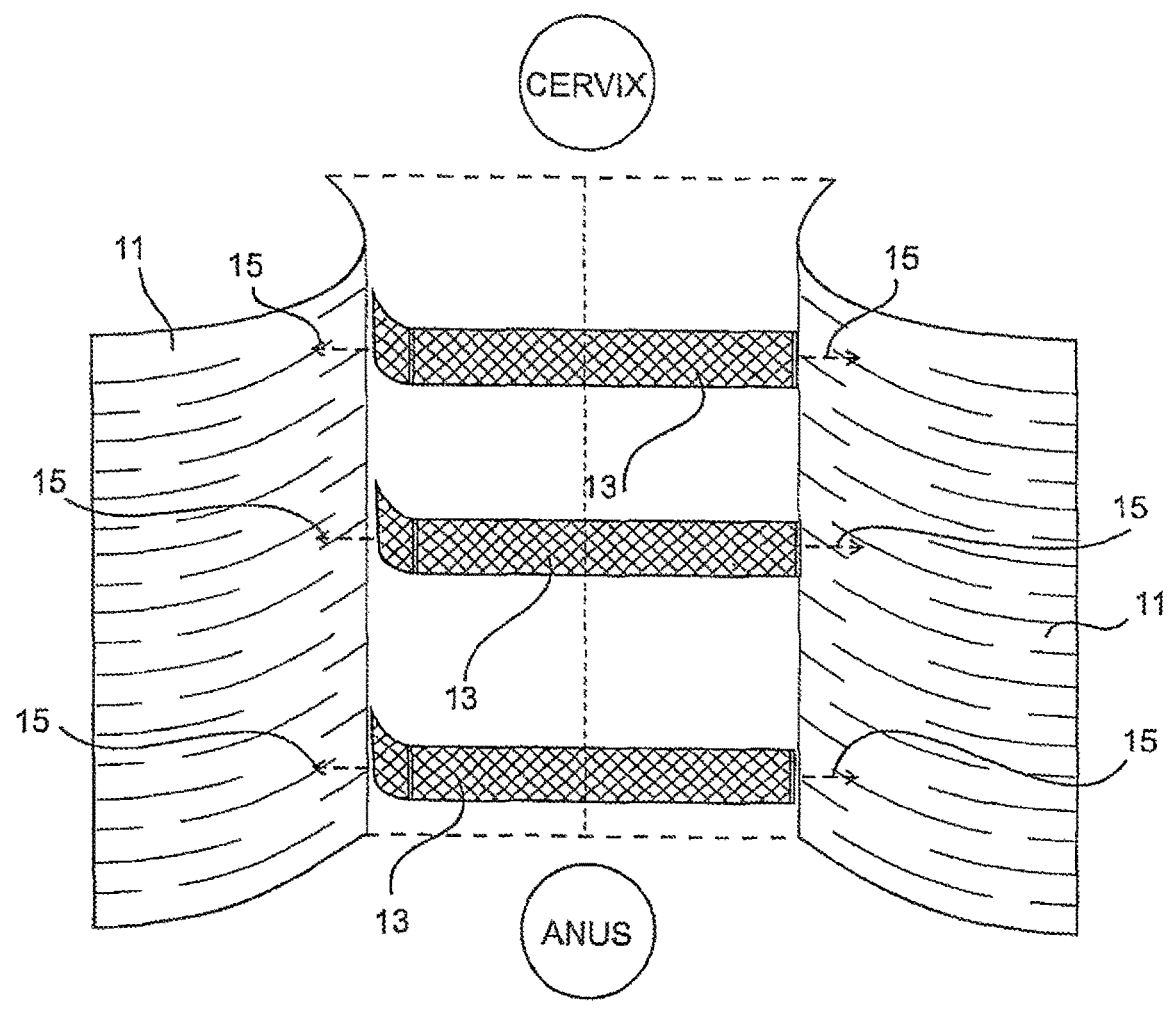
FIG. 1 is a schematic view of the posterior vaginal wall repair according to the first embodiment.
Figure 2:
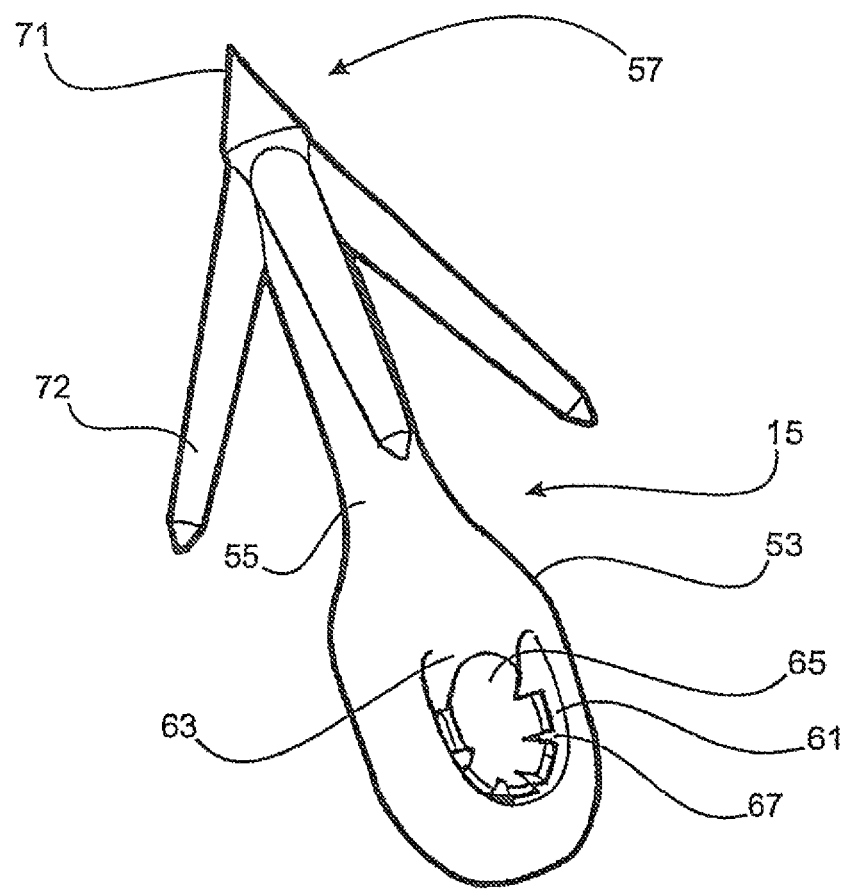
FIG. 2 is an isometric view of an anchor according to the second embodiment.
Figure 3:
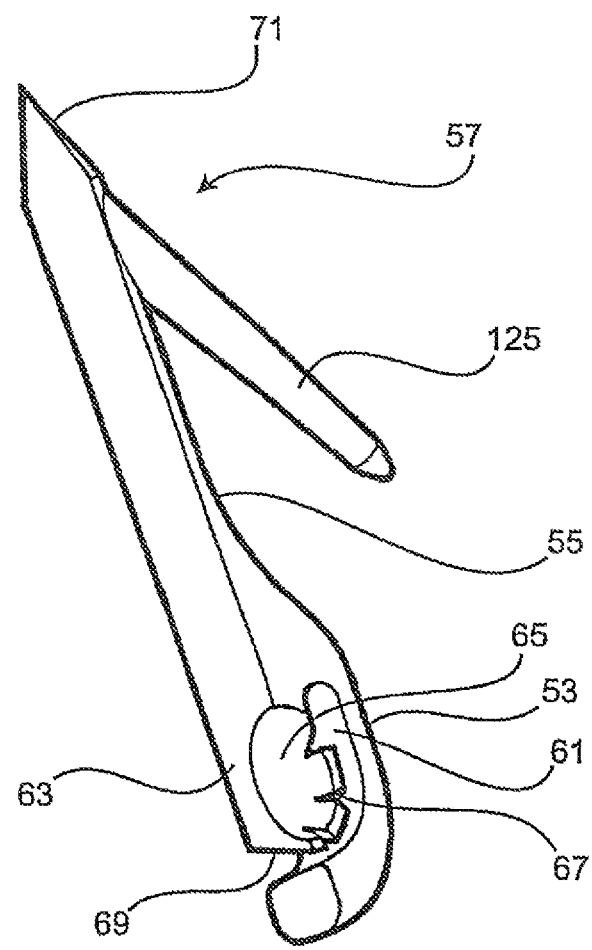
FIG. 3 is a sectional isometric view of the anchor of the second embodiment.

As shown in schematically at FIG. 1 the procedure according to the first embodiment involves forming a longitudinal incision in the anterior and/or posterior vaginal wall. This results in the creation of a pair of flaps 11 of fascial tissue to each side of the longitudinal incision. One or more lengths of filamentary element 13 are then fixed to each of either the recto-vaginal ligaments or the arcus tendineus (A.T.F.P.) ligaments which are located to each side of the vagina. The fixing of each length of filament is effected through a pair of anchors 15 of the form described below which receive the ends of the length of filament whereby because of the nature of the attachment means the spacing between the anchors 15 on the length of filamentary element 13 can be reduced by causing the filamentary element to be drawn through the attachment means of the anchor. The spacing between the anchors on the filamentary element cannot be increased. The anchors 15 on each length of filamentary element 13 are embedded into the recto-vaginal ligaments in opposed relationship to each side of the vagina. Once the anchors 15 are attached, the nature of the attachment means of the anchors enables the length of the filament 13 between the ligaments to be reduced and to introduce a degree of tension into the filamentary element between the ligaments. The flaps 11 of fascial tissue are then resutured into place. With the healing of the incisions the filamentary element becomes embodied into the fascial tissue on the anterior and posterior sides of the vaginal walls to provide reinforcement and support for that fascial tissue.

The tensioning of the filamentary element on its location in position between the recto-vaginal ligaments or the arcus tendineus (A.T.F.P.) ligaments enables the filamentary element to be precisely and sufficiently tightened to bring the fascia towards the mid-line and in so doing serves to repair any hernia. This serves to restore support for the vaginal wall and to facilitate the desired transmission of the muscle contraction to effect opening and closure of the urethra and anus without the muscle having initially to take up the laxity that previously existed in the connection between the fascial tissue and the recto-vaginal ligaments.

Each of the remaining embodiments are directed to an anchor which can be utilised in association with a filamentary element to enable the fixing and location of the filamentary element into a patient as described above in relation to the first embodiment.

The filamentary element which is used in the first embodiment and with which the second and third embodiments are used comprises a tape which is formed of a knitted or woven material where the material once located in the body will facilitate the growth of scar-like tissue upon it The anchor 15 according to the second embodiment is shown at FIGS. 2 to 5. The anchor is formed integrally of a suitable plastics material which may be biodegradable and comprises a base 53, a stem 55 which extends from the base 53 and a head 57 which is supported in spaced relation from the base 53 by the stem 55. The base is of a generally laminar configuration wherein the major faces of the base are substantially planar and parallel to the central axis of the stem 55. The base is formed with an aperture 61 which extends between the faces and which is associated with a locking member 63 which extends from the side of the aperture proximate the head 57 to terminate closely adjacent the other side of the aperture. The free end of the locking member has a convex arcuate configuration to cooperate with the other side of the aperture to define a part annular space. The spacing between the other side of the aperture and the free end of locking member approximately corresponds with the thickness of the filamentary element with which the anchor is to be used, when the filamentary element is tensioned.

The junction of the locking member with the one side of the aperture is such that the locking member can flex laterally out of the plane of aperture in one direction but is resistant to movement out of the plane aperture in the other direction. This selective flexing of the locking member is achieved by forming the one face of the locking member 63 which faces the one direction with a recess 65 which has a boundary adjacent the junction. In addition the edge of the locking member 63 in the region adjacent the space is formed with a set of spaced slots 67 which extend from the one face partially across the end face of the locking member and which define a set of teeth at that edge. In addition the end face 69 of the locking member is divergent away from the other face of the aperture in the opposite direction. The function of the selective flexing of the locking member 63 and the configuration of the teeth is to permit the filamentary element to be able to be pulled through the space between the locking member and the one side of the aperture in the one direction and to prevent movement of the filamentary element through the same space in the opposite direction. The engagement of the filamentary element by the locking member when the filamentary element is moving in the opposite direction is enhanced by the part annular configuration of the space through which the filamentary material is required to pass which causes the filamentary element to furrow in its passage through the space and thus engage with the free edge of the locking member. The divergent nature of the end face 69 serves to guide and enable the movement of the filamentary element in the one direction.

The head 57 of the second embodiment comprises an outer portion 71 which has a pointed conical configuration. In addition the head 57 has a barbed configuration which is provided by a set of prongs 72 which extend rearwardly from the outer portion 71 in a divergent relationship to each other. The arms 69 are spaced angularly equi-distant around the central axis of the stem 55 and each of the arms are of a generally tapered configuration with their outer ends being more convergent than the main portion of each prong 72. Because of the nature of the plastics material of which the anchor is formed the prongs are capable of resilient flexing along their length and at their junction with the stem.

Figure 4:
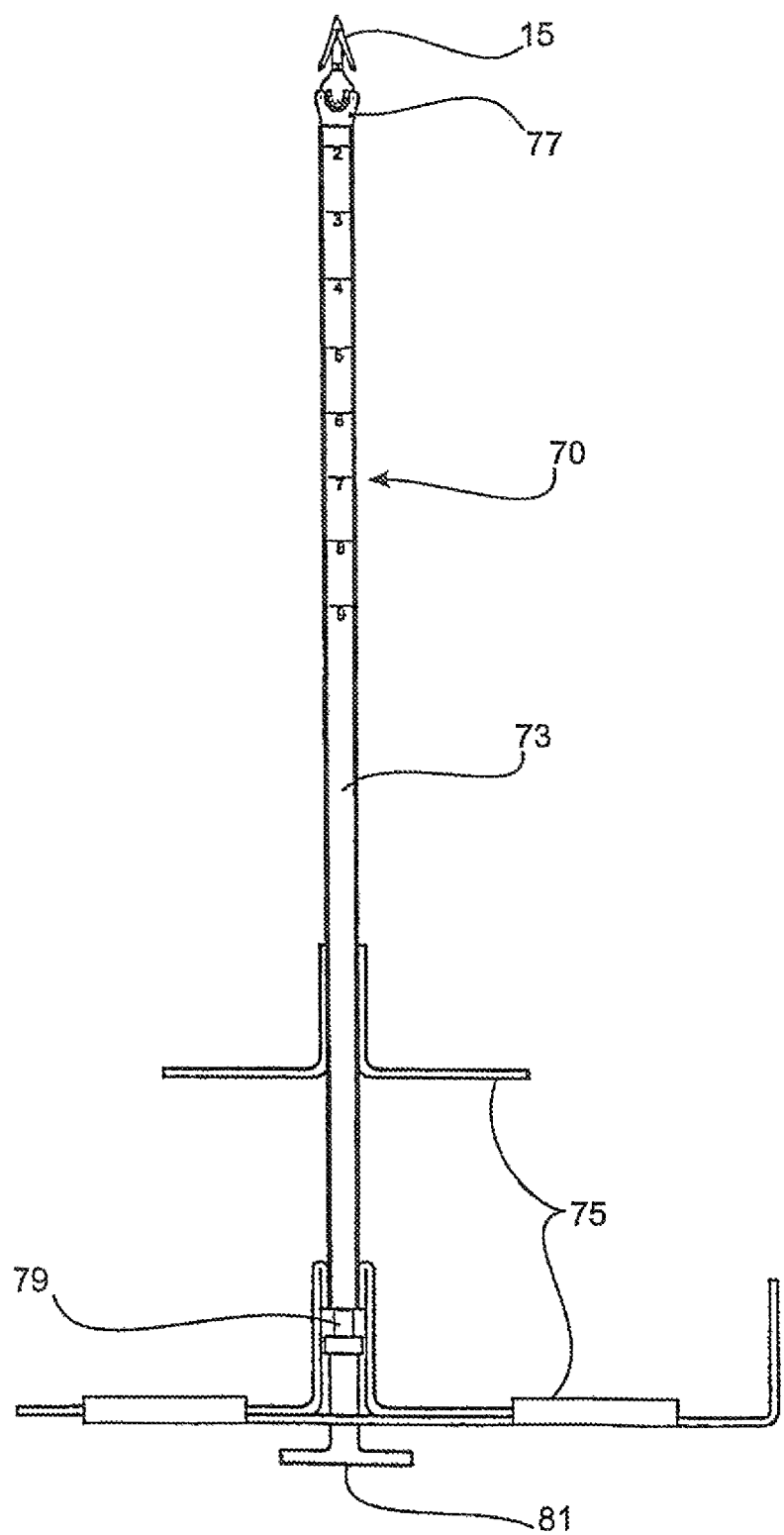
FIG. 4 is a side elevation of an insertion tool intended for use with the anchor of the second embodiment.
Figure 5:
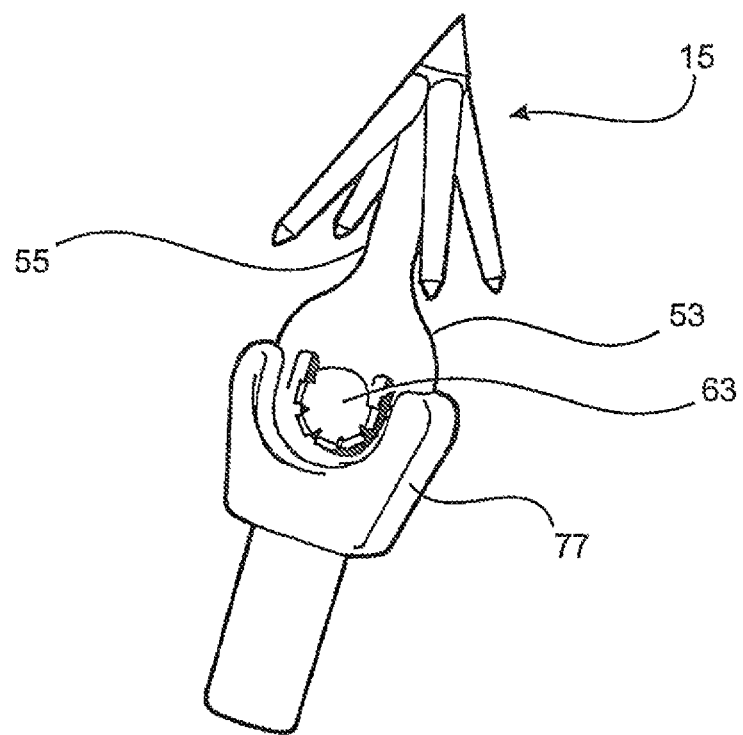
FIG. 5 is an enlarged isometric view of the end of the insertion tool supporting an anchor according to the second embodiment.
Figure 6:
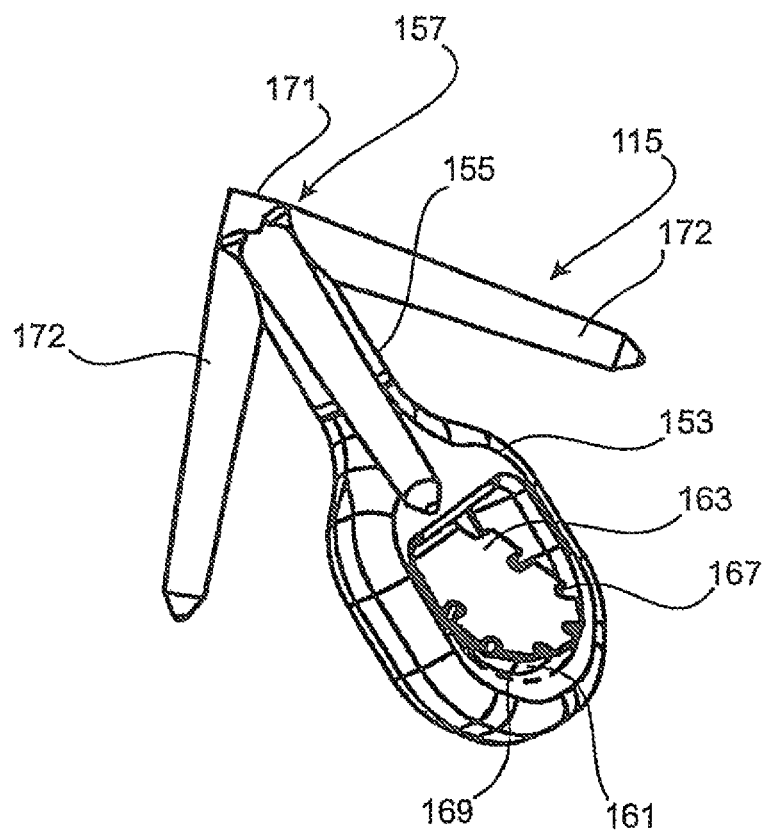
FIG. 6 is an isometric view of an anchor according to the third embodiment.

In use the anchor 15 of the second embodiment is intended to be attached to a length of the filamentary element (not shown) and the filamentary element is inserted into the body of a patient by utilisation of an insertion appliance 70 which is illustrated at FIGS. 4 and 5. The insertion appliance comprises a tubular body 73 which is provided at one end with a handle 75 and at the other end with a cradle-like support 77. The cradle-like support 77 is configured to receive the base of the anchor 15 of the second embodiment and support the anchor as shown at FIGS. 4 and 5 with the head 71 extending axially away from the end of the appliance. The internal bore of the insertion tube slidably supports a pushrod 79 which extends from the one end of the tubular body and is provided with an enlarged head 81 at its outer end The other end of the pushrod is received through a passageway through the cradle-like support 77 to terminate closely adjacent the anchor when supported in the cradle-like support 77. A suitable biasing means is provided between the tubular body 73 and the pushrod 79 to bias the pushrod to its outermost position with respect to the tubular body 73.

In use the anchor 15 is located in the cradle-like support 77 of the insertion tube and the filamentary element (not shown) is initially passed through the aperture of the anchor. The insertion tube 73 is then inserted into the body cavity through an opening in the body wall such that the free end of the insertion tube with the anchor located thereon is located against the surface of a layer of muscle tissue. With the application of an inward axial force on the enlarged head 81 of the pushrod 79, the anchor 15 is caused pass into the muscular tissue to become lodged therein. Because of the pointed configuration of the outer portion 71 of the head, the anchor 15 will move readily into engagement with the tissue, however because of the divergent nature of the arms 25, dislodgement of the anchor from the tissue is restricted. Once the anchor is firmly in position pressure is applied to the enlarged head 81 of the pushrod to displace the anchor from the cradle-like support and then the insertion appliance 70 can be removed from the body to leave the anchor and filamentary element 27 in place. A second anchor is engaged with the filamentary element at its other end and the second anchor is then fixed to another location in a similar manner using the insertion appliance. Because the filamentary element is only capable of movement through the aperture of the anchors in one direction, the length of the filamentary element supported between the anchors can be reduced, to reduce the spacing between the locations and can be tensioned.

Where the filamentary element is used to provide a sling-like support between two anchors supported in the recto-vaginal ligaments as described in relation to the first embodiment the tensioning applied to the filamentary element is such as to restore the normal tension which is expected at the at site to enable the muscular action which is available to be used to control the urethra.

The anchor 115 according to the third embodiment is shown at FIGS. 6 to 13. The anchor is formed integrally of a suitable plastics material which may be biodegradable and comprises a base 153, a stem 155 which extends from the base 153 and a head 157 which is supported in spaced relation from the base 153 by the stem 155 (at a reduced spacing compared to the second embodiment). The base is of a generally laminar configuration wherein the major faces of the base are substantially planar and parallel to the central axis of the stem 155. The base is formed with an aperture 161 which extends between the faces and which is associated with a locking member 163 which extends from the side of the aperture proximate the head 157 to terminate closely adjacent the other side of the aperture. The locking member 163 is substantially planar and is inclined with respect to the central transverse plane of the base from one face to the other face. The free edge of the locking member has a convex arcuate configuration to cooperate with the other side of the aperture to define a part annular space. The spacing between the other side of the aperture and the free edge of locking member approximately corresponds with the thickness of the filamentary element with which the anchor is to be used when the filamentary element is tensioned.

Figure 9:
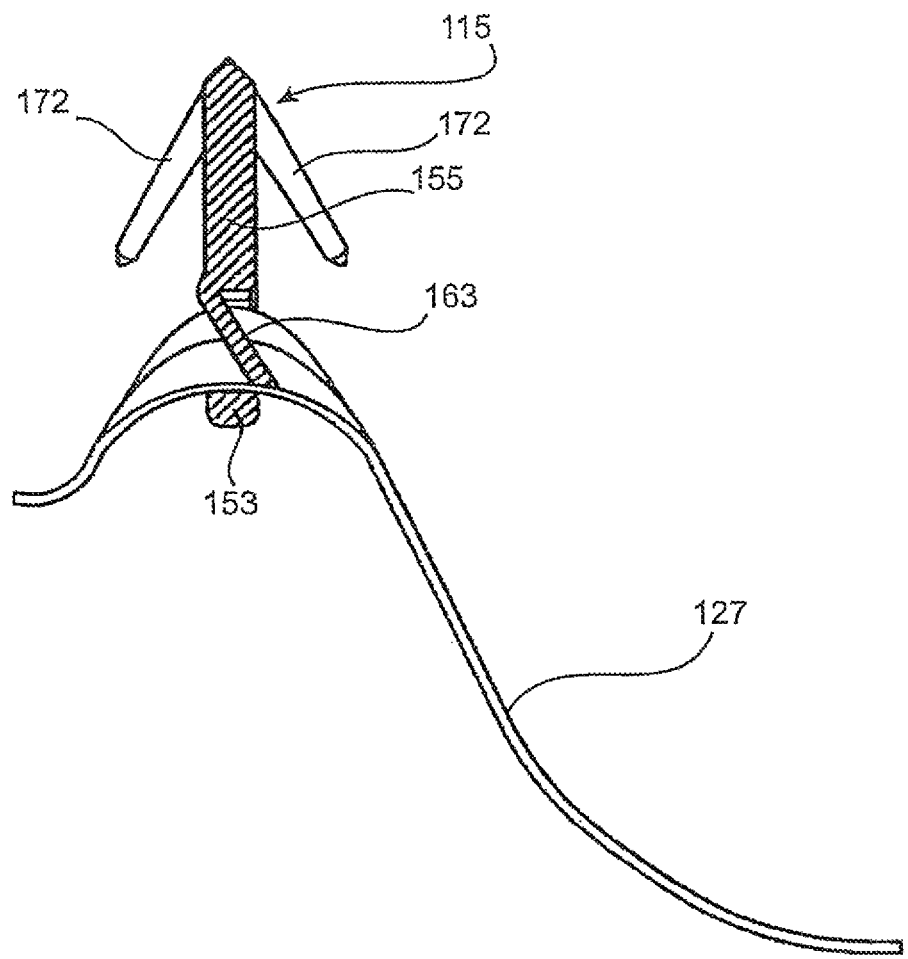
FIG. 9 is a sectional elevation of an anchor according to the third embodiment illustrating engagement between the anchor and a filamentary element.
Figure 10:
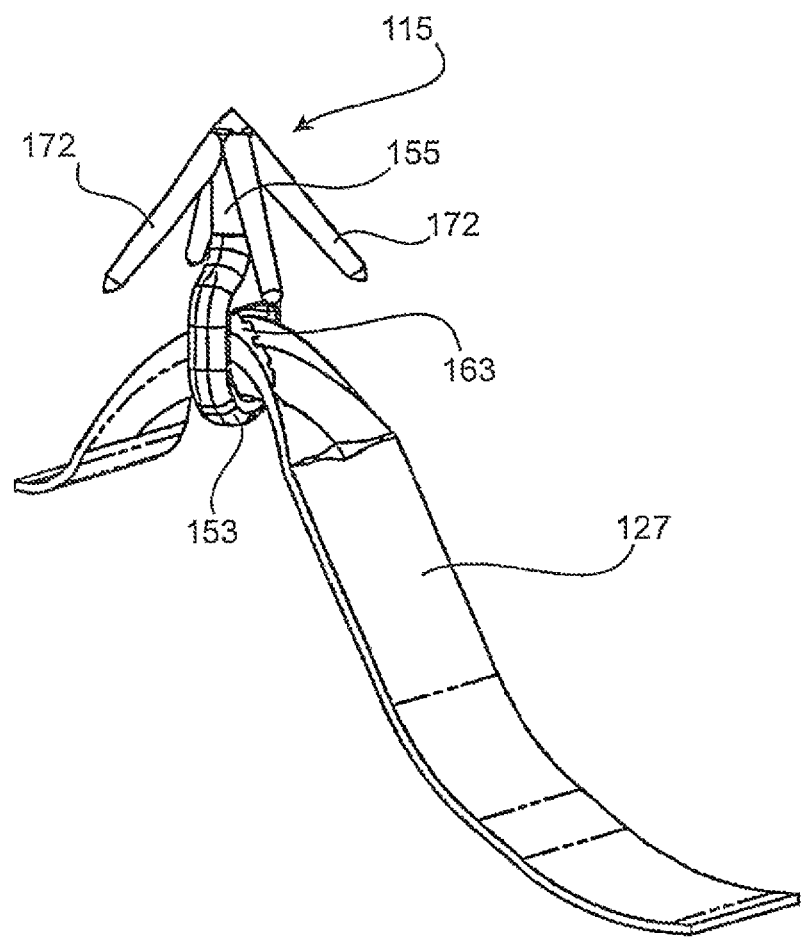
FIG. 10 is an isometric view of an anchor according to the third embodiment engaged with a filamentary element.

The locking member is of a reduced thickness compared to the thickness of the base and as a result the locking member can flex within the aperture. In addition the edge of the locking member 163 in the region adjacent the space is formed with a set of angularly spaced slots 167 which extend from the one face partially across the end face 169 of the locking member to define a set of teeth at that edge. In addition the end face 169 of the locking member is divergent away from the other face of the aperture in the opposite direction. The flexing of the locking member 163, the configuration of the teeth 167 and the configuration of the end face 169 permit the filamentary element 127 to be able to be pulled through the space between the locking member and the one side of the aperture in the one direction with substantially little interference. The divergent nature of the end face 169 serves to guide and enable the movement of the filamentary element in the one direction. In addition when the filamentary element 127 is moving in the one direction it is anticipated that it will be in a state of tension and as a result it is expected that the locking member will not interfere with the filamentary element 127 when it is moving in the one direction since the dimensions of the space will correspond with the cross section of the tensioned filamentary element 127 passing through it. However the flexing of the locking member 163, the configuration of the teeth 167 and the configuration of the end face 169 also serve to, prevent movement of the filamentary element 127 through the same space in the opposite direction. The engagement of the filamentary element 127 by the locking member when the filamentary element 127 is moving in the opposite direction is enhanced by the part annular configuration of the space through which the filamentary element 127 is required to pass which causes the filamentary element 127 to furrow in its passage through the space and thus engage with the free edge of the locking member as shown at FIGS. 9 and 10. When the filamentary element 127 is caused to move in the opposite direction the portion of the element approaching the aperture will generally not be in tension and this condition of the element together with the configuration of the space, serves to further enhance the interference that the locking member creates for movement of the filamentary element. In addition in the light of the inclined orientation of the locking member across the aperture, on movement of the filamentary element through the space in the opposite direction the interference therebetween will cause the free end of the locking member to move resiliently towards the opposite edge of the aperture and clampingly engage the filamentary element therebetween. Therefore the relationship between the locking member and the aperture serves to positively prevent the filamentary element 127 from movement in the opposite direction through the space.

The head 157 of the third embodiment comprises an outer portion 171 which has a pointed conical configuration. In addition the head 157 has a barbed configuration which is provided by a set of prongs 172 which extend rearwardly from the outer portion 171 in a divergent relationship to each other. The arms 169 are spaced angularly equidistant around the central axis of the stem 155 and each of the arms are of a generally tapered configuration with their outer ends being more convergent than the main portion of each prong 172. Because of the nature of the plastics material of which the anchor is formed the prongs are capable of resilient flexing along their length and at their junction with the stem.

Figure 12:
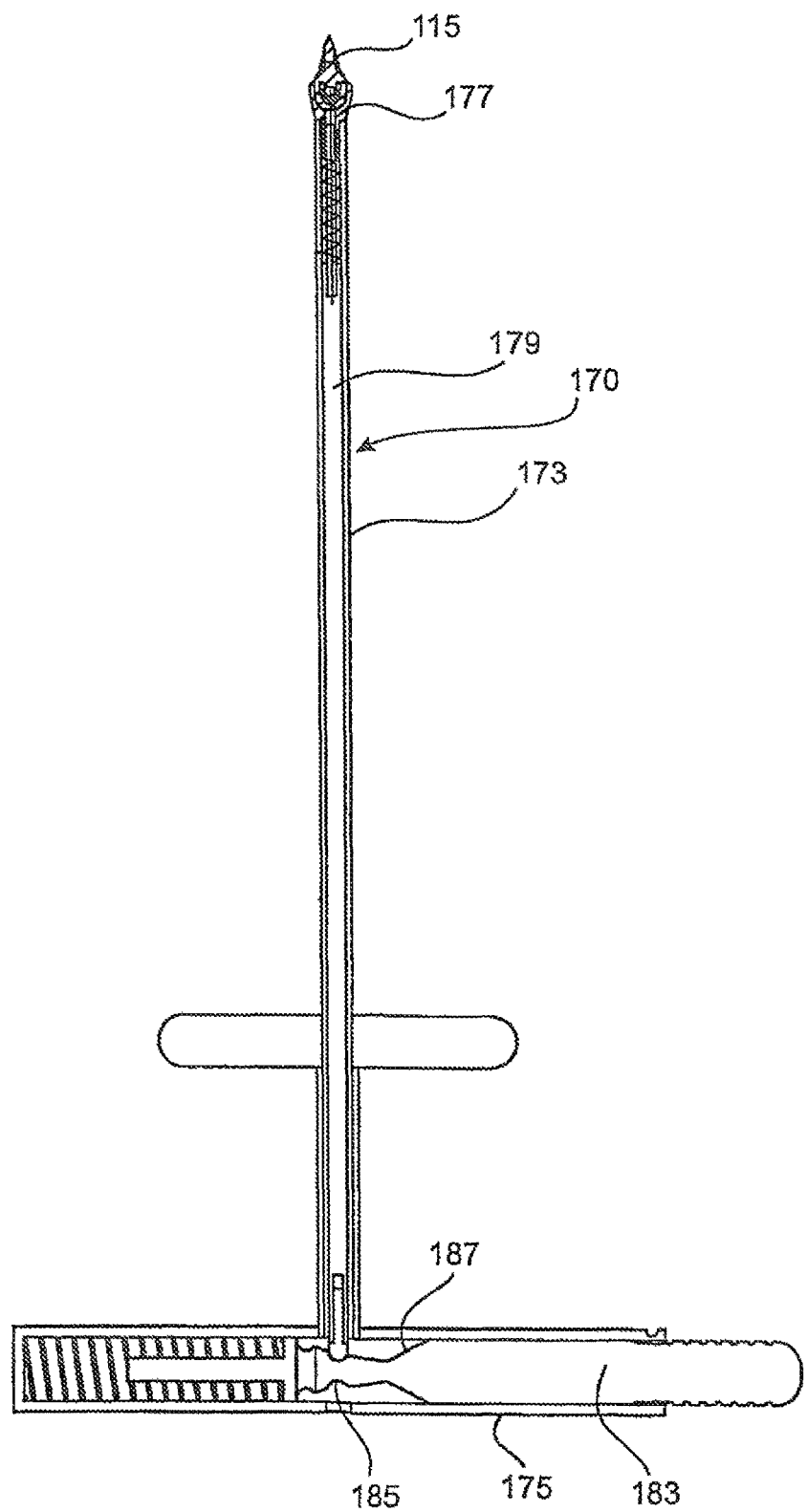
FIG. 12 is a sectional side elevation of an insertion appliance according to the third embodiment.

In use the anchor 115 of the third embodiment is intended to be attached to a length of the filamentary element as shown at FIGS. 9 and 10 and the filamentary element is inserted into the body of a patient by utilisation of an insertion appliance 170 which is illustrated at FIG. 12. The insertion appliance comprises a tubular body 173 which is provided at one end with a handle 175 and at the other end is adapted to receive a cradle-like support 177. The cradle-like support 177 is configured to receive the base of the anchor 115 of the third embodiment and support the anchor as shown at FIGS. 6 to 10 with the head 171 extending axially away from the end of the appliance. The cradle-like support is described in greater detail below. The internal bore of the insertion tube slidably supports a pushrod 179 which extends from the one end of the tubular body into the interior of the handle 175. The other end of the pushrod is received through a passageway through the cradle-like support 177 to terminate closely adjacent the anchor when supported in the cradle-like support 177. A suitable biasing means is provided between the tubular body 173 and the pushrod 179 to bias the pushrod towards the handle. The handle slidably receives a rod-shaped plunger 183 and the outer end of the pushrod 179 bears on the plunger 18. The portion of the surface of the plunger which receives the pushrod is profiled with a notched portion 185 which receives the outer end of the pushrod when in its retracted position and with an increased diameter portion 187 which will receive the outer end of the pushrod when the plunger is pushed axially inwardly into the handle to cause the pushrod to move to its extended position. When the pushrod is at its extended position it will bear upon anchor 115 supported on the cradle-like support 177 to force the anchor out of engagement with the cradle-like support 177.

Figure 11:
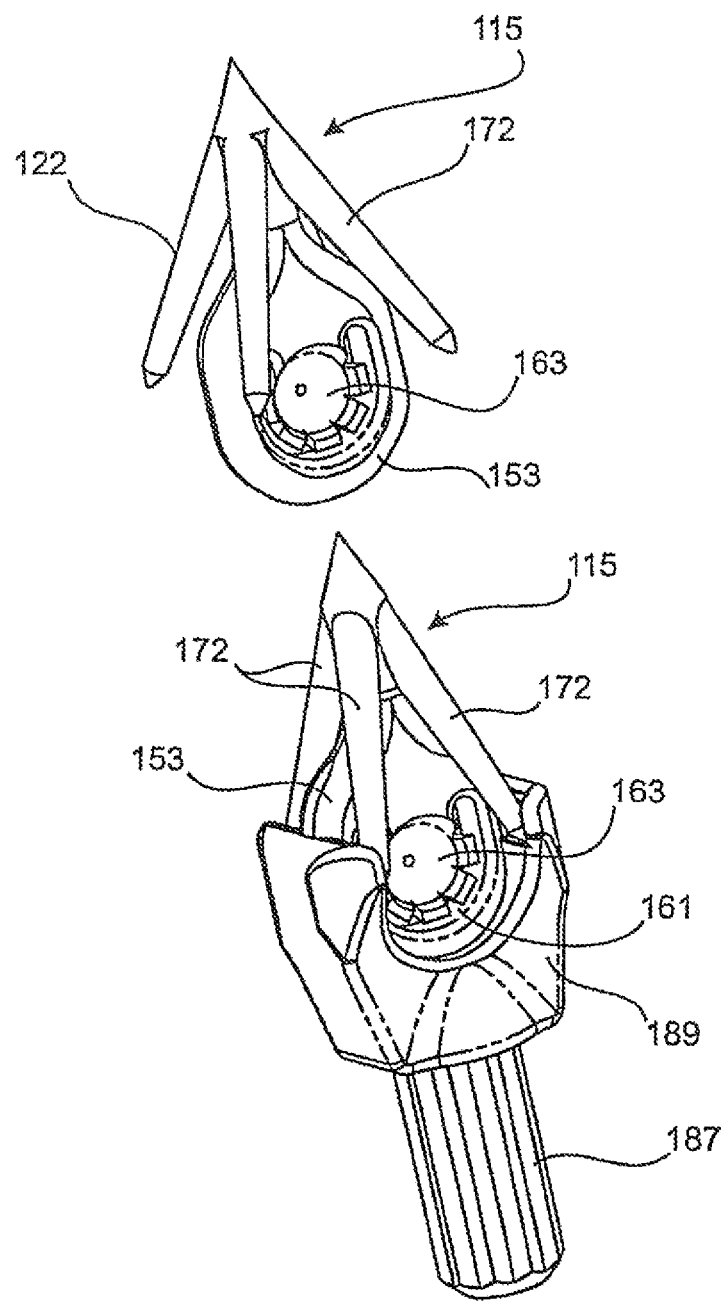
FIG. 11 is an isometric view of an anchor according to the third embodiment in engagement with a cradle like support and also illustrating the anchor out of engagement with the cradle like support.

As shown at FIG. 11 the cradle-like support comprises a central spigot 187 which is intended to be received in the end of the tubular body 173 and is configured to be frictionally engaged in the end. The outer end of the spigot supports cradle 189 which is shaped to support the base 153 of an anchor at the sides. The cradle is recessed to provide free access to the aperture 161. In addition the sides of the recess are configured at their outer ends to receive and support the free ends of the prongs 172 when compressed radially relative to each other as shown at FIG. 11. The cradle-like support is formed with a central passage which receives the pushrod 179 of the insertion appliance whereby when the pushrod is at its extended position it bears upon the base of the anchor to force it out of engagement with the cradle 189. When the anchor is free of the cradle-like support the free ends of the prongs are able to expand radially.

Figure 13:
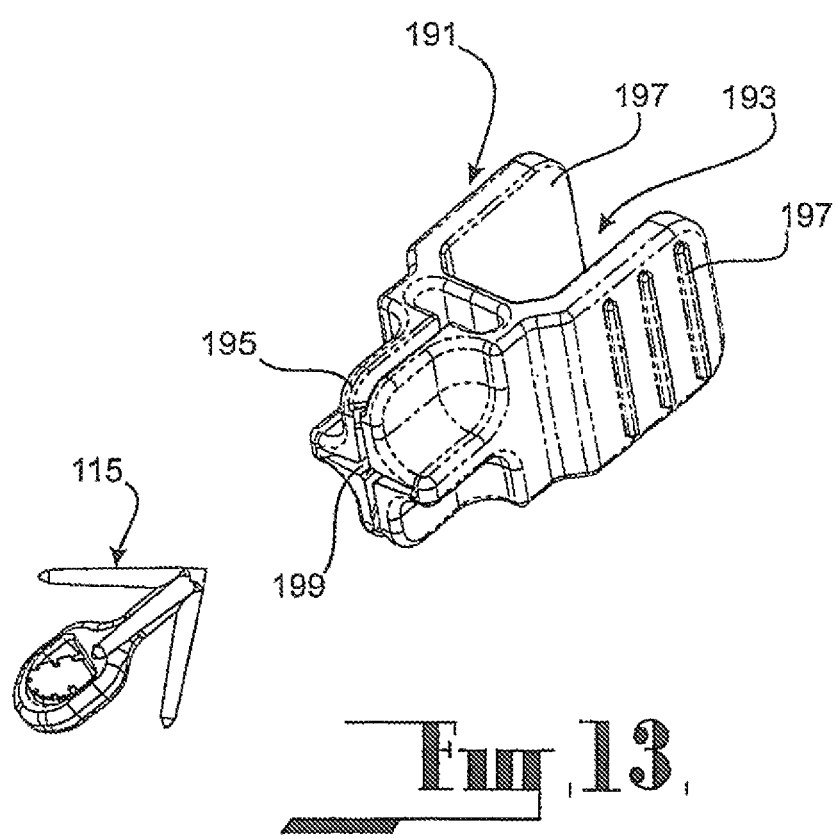
FIG. 13 is an isometric view of anchor and a holder according to the third embodiment.

To locate the anchor in position on the cradle-like support, a holder 191 of the form shown at FIG. 13 is used. The holder comprises body having a grip 193 at one end and an anchor support 195 at the other end. The grip 193 comprises a pair of opposed tabs 197 which are dimensioned and spaced from each other to be able to be engaged between a finger and thumb of the operator. The anchor support comprises a cross-like recess 199 which is configured to receive the head of the anchor, including the prongs and in so doing to radially compress the free ends of the prongs in order that they can be received in the cradle 189 of the cradle-like support.

In use the head of an anchor 115 is located in the recess of the holder and is then transferred to the cradle-like support 177 to be supported therein. This location and transfer of the anchor can be effected using the holder and without manually handling the anchor. The anchor pre-loaded with the filamentary element is supported in the cradle-like support. The insertion tube 173 is then inserted into the body cavity of the patient through an opening in the body wall such that the free end of the insertion tube with the anchor located thereon is located against the surface of a layer of muscle tissue. On application of additional force the head of the anchor as well as a portion of the cradle-like support is introduced into the muscle tissue. With the depression of the plunger of the insertion appliance, the pushrod 179 forces the anchor out of engagement with the cradle-like support to be received in the muscle tissue and to become lodged therein. The radial expansion of the free ends of the prongs when free of the cradle further serve to ensure retention of the anchor in the tissue. Because of the pointed configuration of the outer portion 171 of the head, the anchor 115 will move readily into engagement with the tissue, however because of the divergent nature of the prongs 125, dislodgement of the anchor from the tissue is restricted. The retention of the free ends of the prongs in the cradle enables the operator some degree of freedom in locating the anchor and the prongs are only released when the operator is satisfied with the location of the anchor. Once the anchor is firmly in position the insertion appliance 171 can be removed from the body to leave the anchor and filamentary element 127 in place. A second anchor at the other end of the filamentary element is then fixed to another location in a similar manner using the insertion appliance. Because the filamentary element is only capable of movement through the aperture of the anchors in one direction, the length of the filamentary element supported between the anchors can be reduced, to reduce the spacing between the locations and can be tensioned.

Where the filamentary element is used to provide a sling-like support between two anchors supported in the recto-vaginal ligaments as described in relation to the first embodiment the tensioning applied to the filamentary element is such as to restore the normal tension which is expected at the at site enable the muscular action which is available to be used to control the urethra.

Figure 14:
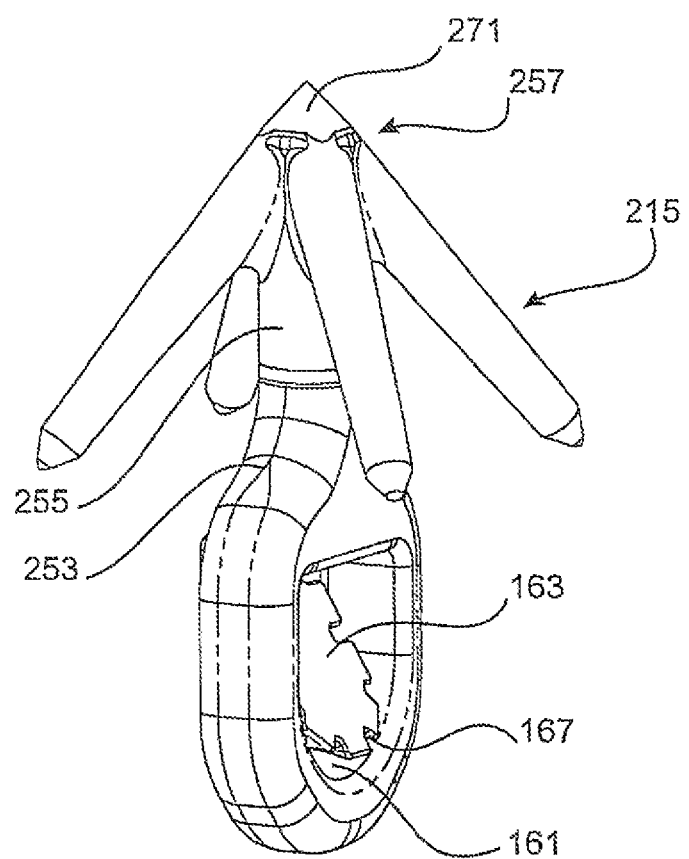
FIG. 14 is an isometric view of anchor according to the fourth embodiment.
Figure 15:
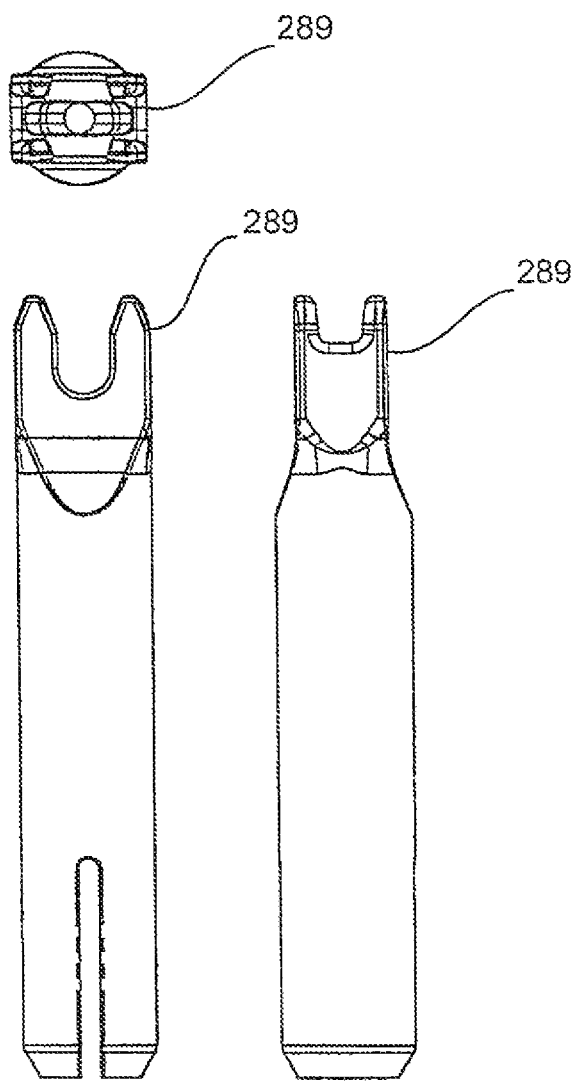
FIG. 15 is an end elevation and two side elevation of a cradle like support according to the fourth embodiment.
Figure 17:
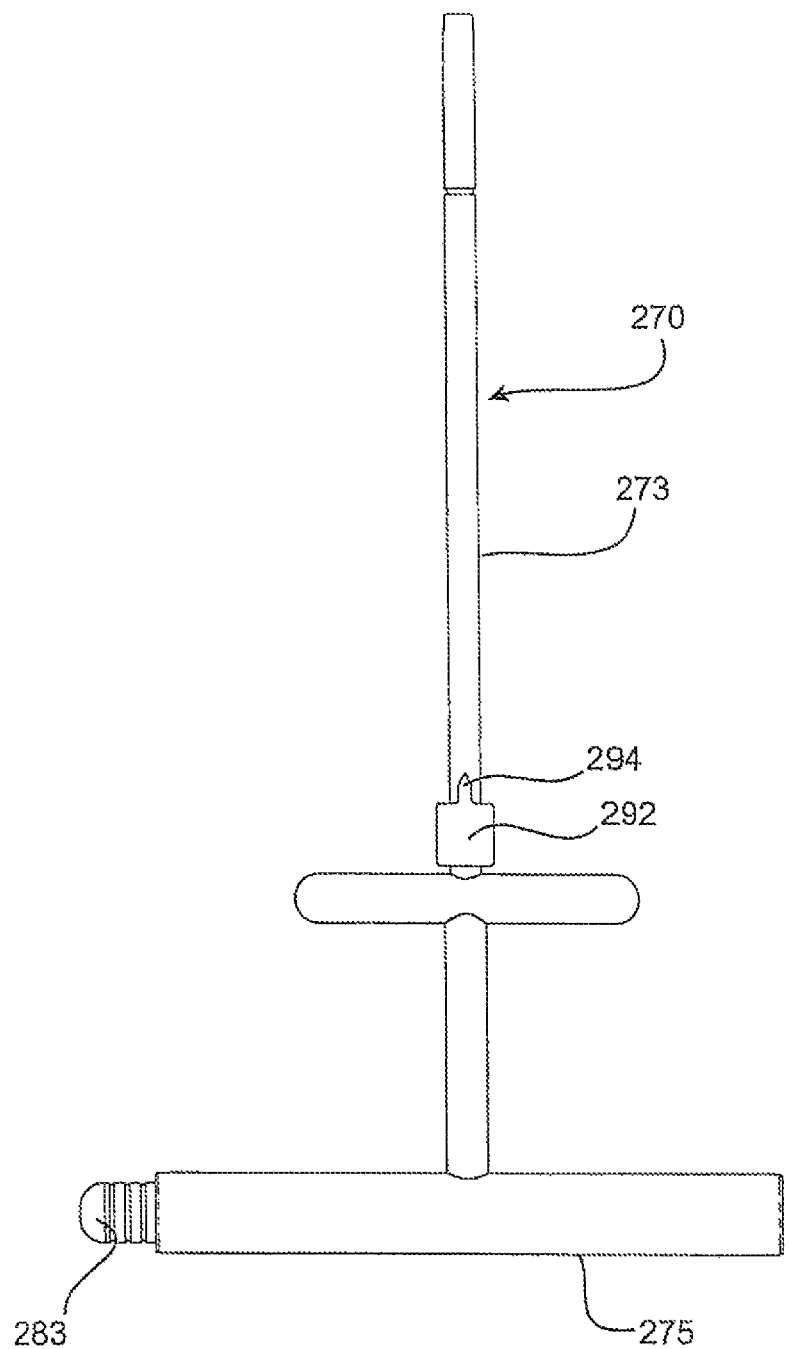
FIG. 17 is a side elevation of an insertion appliance according to the fourth embodiment.
Figure 18:
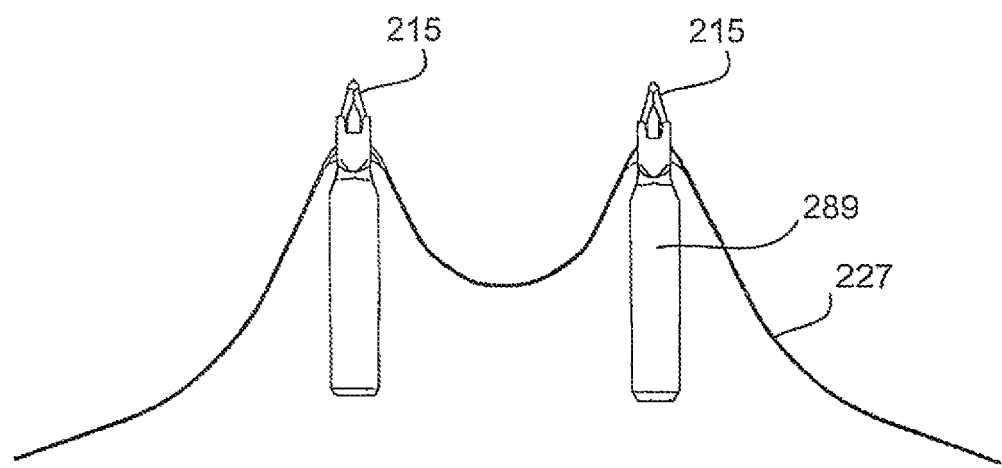
FIG. 18 is an illustration of a pair of holder like supports each accommodating an anchor which in turn is received on a filamentary element.
Figure 19:
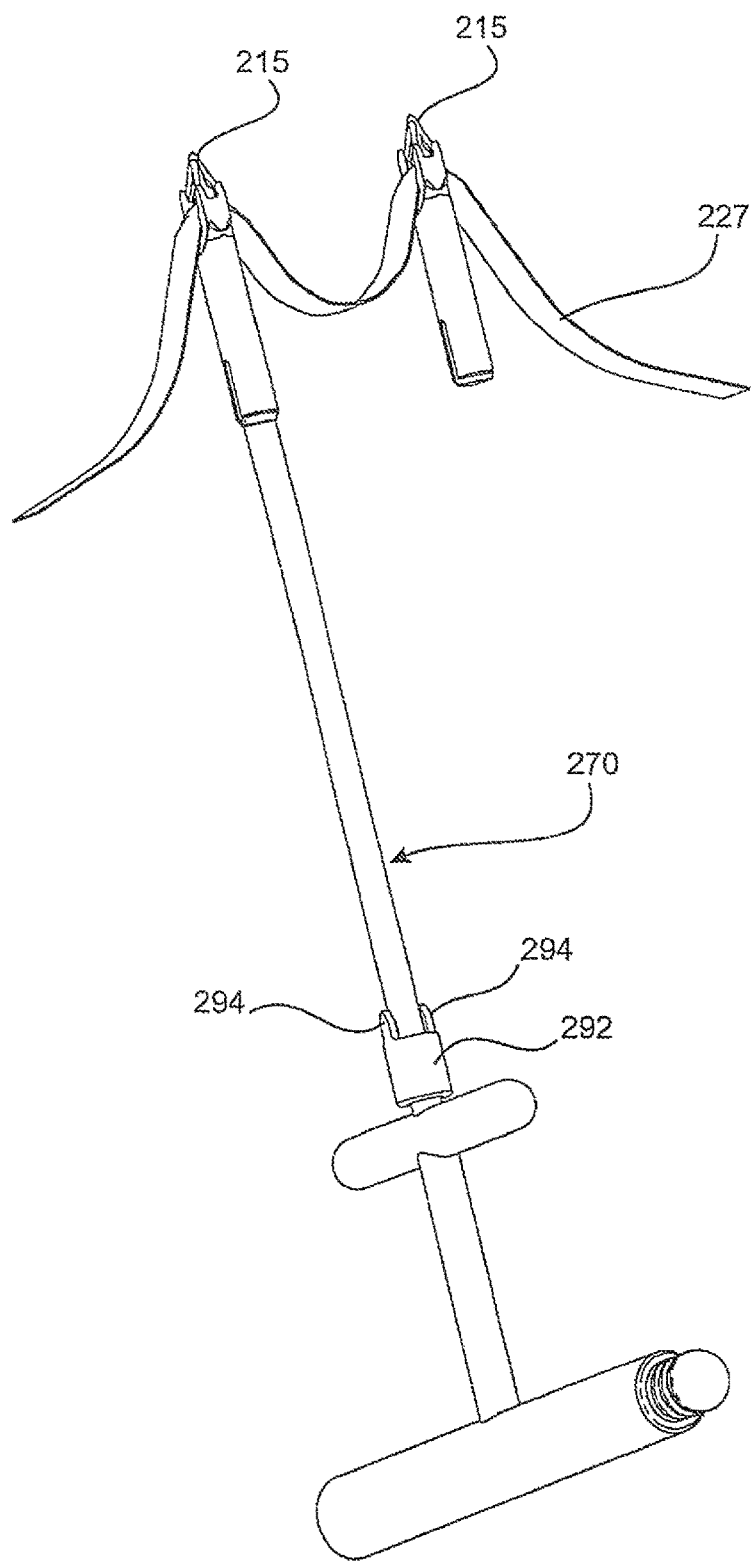
FIG. 19 is illustrative of the initial step involved in operation of the anchor for insertion.

According to a fourth embodiment as illustrated at FIGS. 14 to 21 an anchor 215 of the form as shown at FIG. 14 and which generally corresponds with an anchor according to the third embodiment is applied to a cradle-like support 277. As illustrated in FIGS. 15 and 16 the cradle-like support 277 is formed as a tubular element which is receivable over the outer end of insertion tool 270 and is formed at one end with a cradle like portion which will support and engage the anchor 215 in a similar manner to that described in relation to the third embodiment and as shown in the accompanying drawings. The configuration of the insertion appliance 270 is of the same form as that of the third embodiment. The tubular portion of the cradle-like support is formed towards its other end to be of a bifurcated configuration to allow for resilient flexing between the bifurcated portions of the tubular portion so defined when other end of the cradle-like support is applied over the outer end of the insertion appliance in order that they clampingly engage the outer surface of the tubular portion at 273 of the insertion appliance 270. If desired suitable detents may be provided in the wall of the tubular portion 273 to retain the cradle-like support in position on the end of the insertion appliance.

In addition the insertion appliance 270 is provided with a collar 292 which is slidable on the tubular portion of the insertion appliance 270. The collar 292 is provided with a pair of diametrically opposed prongs 294 which will engage in the slots between the bifurcations of the cradle-like support and with appropriate axial movement of the collar on the tubular member will cause separation between the bifurcations to facilitate removal of the cradle-like support from engagement with the insertion appliance.

Figure 20:
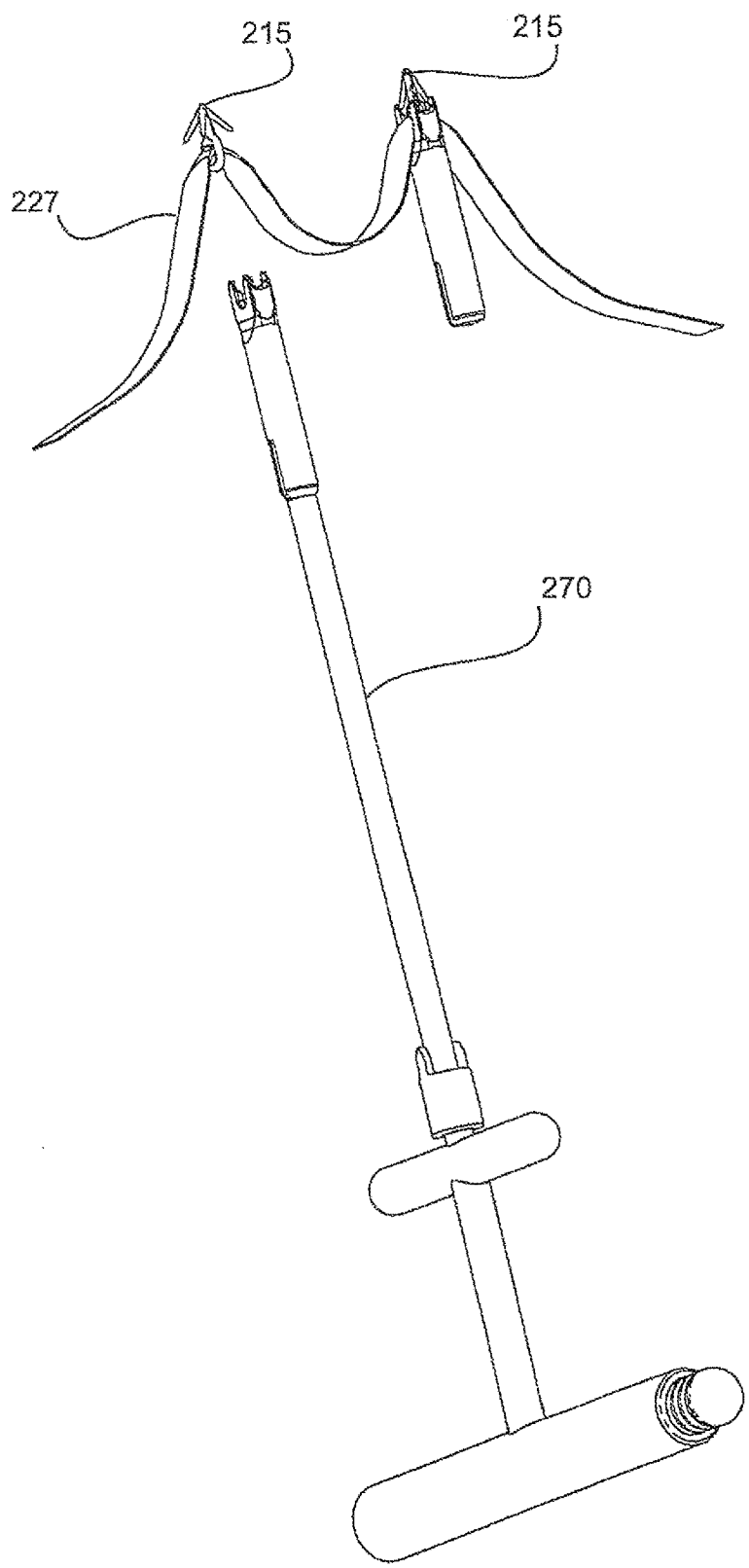
FIG. 20 is an illustrative view of the insertion appliance subsequent to release of the first anchor.
Figure 21:
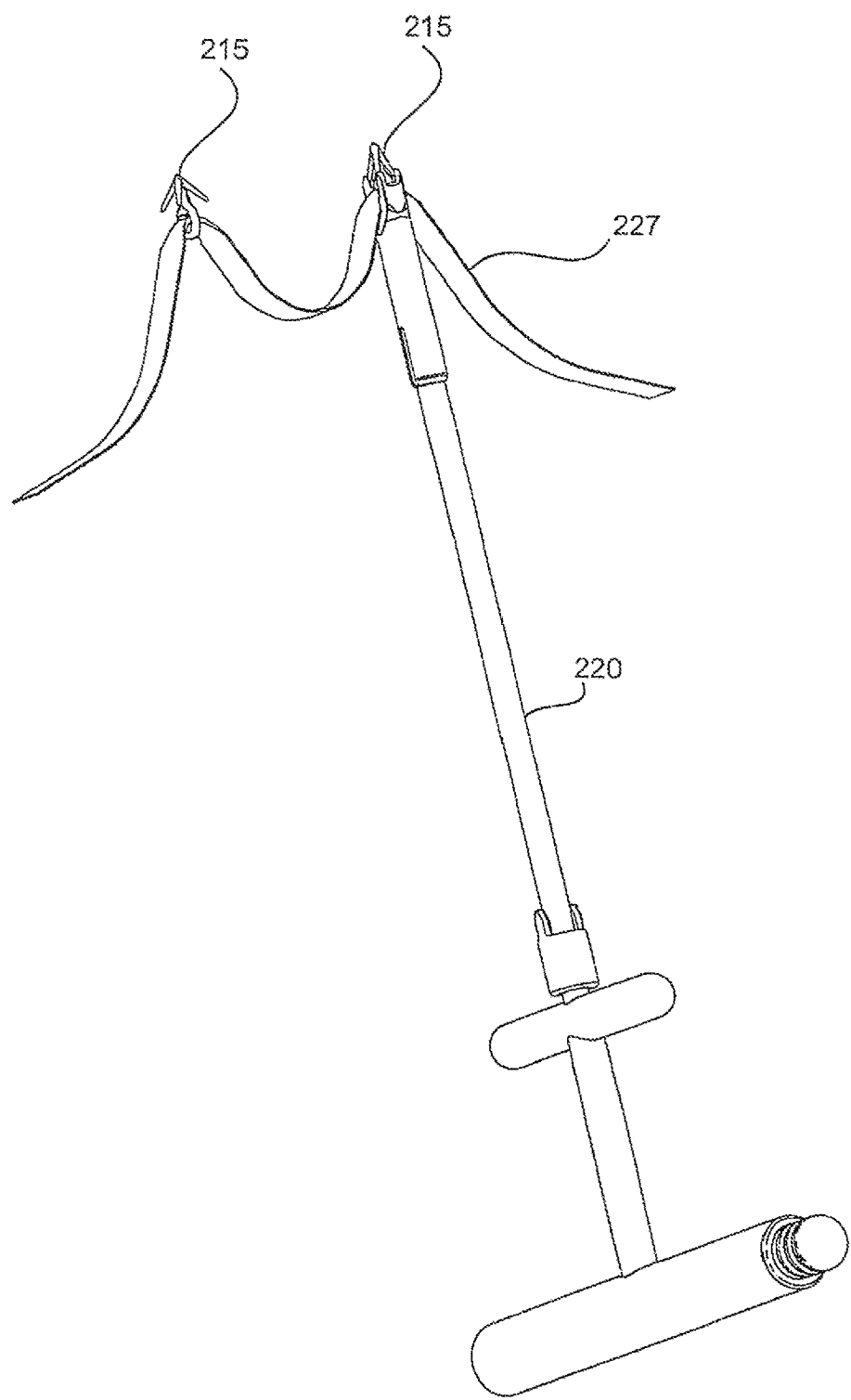
FIG. 21 is a schematic view of an insertion applicant applied to the second anchor.

In use the cradle-like support 277 and the anchor 215 is provided as a single item and it is intended that a pair of composite items be provided on a length of filamentary element 227 as a pre-packaged composite item whereby the anchors 215 are sequentially installed using an insertion tool in a manner as illustrated at FIGS. 20-21.

In an alternative application of the anchors according to the second, third and fourth embodiments they are used to directly shorten a stretched ligament or fascial tissue by inserting a pair of anchors into a ligament at spaced intervals along the ligament and shortening the ligament or fascial tissue by tensioning the filamentary element between the anchors.

Throughout the specification, unless the context requires otherwise, the word "comprise" or variations such as "comprises" or "comprising", will be understood to imply the inclusion of a stated integer or group of integers but not the exclusion of any other integer or group of integers.

It should be appreciated that the scope of the invention need not be limited to the particular scope of the embodiment described above and in particular is not restricted to the particular example of application of the embodiment described above.

The invention claimed is:

1. A method of providing ligamentary-like support between two tissues disposed at spaced locations in the body of a patient, comprising the steps of:
   fixing an anchor to the tissue at each location;
   providing a filamentary element, wherein said anchors include an aperture and at least some of said anchors further include a retaining element, said retaining element being configured to permit said filamentary element to be drawn through said aperture in one direction and to prevent movement of said filamentary element through said aperture in the opposite direction;
   connecting said anchors by passing said filamentary element through the respective apertures of the anchors; and
   adjusting the tension of the filamentary element between the locations by drawing the filamentary element through at least one of the anchors with the retaining element, the retaining element preventing said filamentary element from moving back through said aperture after said filamentary element is released thereby retaining said filamentary element between the anchors in a state of tension, wherein the filamentary element establishes a sling-like support for an organ or other body tissue between the two tissues
   and the filamentary element is retained in the state of tension between the anchors by said retaining element after the filamentary element is released to provide said ligamentary-like support between the tissues.

2. A method according to claim 1 wherein the filamentary element is not biodegradable over a period of time and is adapted to facilitate the growth of tissue on at least part of the filamentary element located between the locations to provide said ligamentary-like support between the locations.

3. A method according to claim 1 wherein one of said anchors has a head having a configuration facilitating insertion into the tissue and retention of the head in the tissue once inserted, said one of said anchors further having a base with two major faces with said aperture extending between said faces, said aperture receiving said filamentary element, said method comprising inserting said head into the respective tissue.

4. A method according to claim 3 wherein the head has a barbed configuration.

5. A method according to claim 4 wherein the barbed configuration comprises a set of prongs extending in a divergent manner from the end of the head towards the base, said prongs being resiliently flexible along their length, said method comprising inserting the head into the tissue and releasing the ends of the prongs once the head is located in the tissue.

6. A method according to claim 5 further comprising compressing the ends of the prongs towards each other prior to the insertion of the head into the tissue.

7. A method according to claim 6 wherein the holder is adapted to receive and support the prongs in their compressed state, said method comprising releasing the prongs from engagement with the holder when the anchor is in position.

8. A method according to claim 5 wherein the anchor is associated with a holder which is configured to retain the anchor with the head directed outwardly from the holder, the method comprising installing an anchor in the holder, placing the anchor in position in the tissue by means of the holder and subsequently disengaging the holder from the anchor.

9. A method according to claim 8 wherein the filamentary element is drawn through the aperture in the anchor and the anchor is installed on the holder prior to insertion of the head into the tissue.

10. A method according to claim 8 further comprising associating the holder with an insertion appliance, the insertion appliance having a shaft, one end of the shaft adapted to receive the holder, the other end of the shaft supporting the handle, an ejection means extending between the handle and the one end and having a bearing member at one end adapted to bear upon one of said anchors when installed in the holder, the handle provided with a manipulation member adapted to cause the bearing member to bear on said one of said anchors and cause the displacement of the anchor from the holder, said method comprising locating the holder at the one end of the shaft, installing said one of said anchors into the holder, placing said one of said anchors in position in the respective tissue by manipulation of the appliance and on location of said one of said anchors in the respective tissue, activation of the manipulation means to cause displacement of said one of said anchors from the holder.

11. A method according to claim 1 wherein the spaced locations are one of the recto-vaginal ligaments or the arcus tendineus ligaments to each side of the vagina or other ligaments/muscle/tissue within the pelvic floor and the method resides in the re-establishing of the fascial support for the vagina, said method comprising fixing said anchors into said one of the recto-vaginal ligaments and the arcus tendineus ligaments respectively to each side of the vagina, applying the filamentary element between the anchors, tensioning the filamentary element between said one of the recto-vaginal ligaments and the arcus tendineus ligaments and introducing the filamentary element into the fascial tissue to provide support to the fascial tissue and with time it will become embodied with the fascia and will further tension the filamentary element between the anchors.

12. A method according to claim 1 wherein the filamentary element is drawn through the aperture of at least one of the anchors prior to fixation.

13. A method according to claim 12 wherein the filamentary element is drawn through the aperture of said anchors prior to fixation at a spacing greater than the desired spatial relationship.

14. A method according to claim 1 wherein each said anchor includes a head embedded in the respective tissue during said step of fixing said anchors, said anchor further including a base with two opposed major surfaces with said aperture extending between said major faces.

15. The method of claim 14 wherein said aperture is formed with an aperture edge and said retaining element extends from said aperture edge.

16. A method of providing ligamentary-like support between two spaced locations in the body of a patient wherein the locations include a respective tissue, said method comprising the steps of:
    fixing an anchor to the tissue at each location, the anchors being connected by a filamentary element, each anchor having an aperture receiving the filamentary element and a retaining element configured to permit the filamentary element to be drawn through the aperture in a first direction and to prevent movement of the filamentary element through the aperture in an opposite direction; and
    tensioning the filamentary element between said locations by drawing the filamentary element through said aperture in said one direction, said tensioned filamentary element being prevented from moving in the opposite direction by said retaining element, wherein the tensioned filamentary element provides the ligamentary-like support between the respective tissues.

17. A method according to claim 16 wherein one of said anchors includes a head that has a barbed configuration, said method including engaging the barbed configuration in the respective tissue.

18. A method according to claim 17 wherein said one of said anchors further includes a base part for engagement with the filamentary element.

19. A method of providing ligamentary-like support between two spaced tissues in the body of a patient comprising the steps of:
    fixing an anchor in each tissue, each anchor including a base with an aperture sized to receive a filamentary element, said base further including a retaining element configured to permit the filamentary element to be drawn through said aperture in one direction and to prevent said filamentary element from being drawn through said aperture in the opposite direction;
    connecting the anchors with the filamentary element by passing said filamentary element through the apertures of said anchors in said one direction;
    adjusting the tension of the filamentary element between the tissues by drawing the filamentary element through the aperture of at least one of the anchors to establish a desired spatial relationship of the filamentary element between the tissues to provide said ligamentary-like support between the tissues;
    wherein said retaining element prevents movement of the filamentary element through the one anchor in an opposite second direction thereby retaining said filamentary element in a tensioned state.

20. A method of providing ligamentary-like support between two spaced tissues in the body of a patient comprising the steps of:
    fixing a first anchor in a first tissue;
    fixing a second anchor in a second tissue, said first and second anchors having respective apertures sized to receive as filamentary element and a retaining element configured to permit the filamentary element to be drawn through said aperture in a first direction, said retaining element further being configured to prevent said filamentary element from being drawn in an opposite direction through said aperture;
    locating said filamentary element between the first and second anchors by passing said filamentary element through the respective apertures of the first and second anchors with respective portions of said filamentary element being engaged by the respective retaining elements of each of said first and second anchors; and
    drawing a part of the filamentary element through the aperture of the first anchor to tension the filamentary element wherein the tensioned filamentary element establishes the ligamentary-like support between the first and second tissues.

21. A method of providing ligamentary-like support between two spaced tissues in the body of a patient, comprising the steps of:
    fixing an anchor in each tissue, the anchors being connected by a filamentary element, each anchor including an aperture receiving said filamentary element and a retaining element formed on said anchor and configured to permit drawing of said filamentary element in one direction through said aperture and preventing said filamentary element from being drawn in an opposite direction; and
    adjusting the tension of the filamentary element between the tissues by pulling said filamentary element through the aperture of at least one anchor after said anchors have been fixed into each tissue to tension said filamentary element and to establishes a sling-like support for a body part of the patient located generally between the tissues whereby the ligamentary-like support is provided.

* * * * *